(12) United States Patent
Engel

(10) Patent No.: US 8,037,883 B2
(45) Date of Patent: Oct. 18, 2011

(54) ORAL DEVICE

(76) Inventor: Harry Engel, Palmdale, CA (US)

( * ) Notice: Subject to any disclaimer, the term of this patent is extended or adjusted under 35 U.S.C. 154(b) by 936 days.

(21) Appl. No.: 11/425,518

(22) Filed: Jun. 21, 2006

(65) Prior Publication Data
US 2007/0295342 A1    Dec. 27, 2007

(51) Int. Cl.
*A61G 15/00* (2006.01)
*A61C 5/14* (2006.01)
*A61C 3/00* (2006.01)
(52) U.S. Cl. .............................. 128/845; 128/861; 433/6
(58) Field of Classification Search .................. 128/862, 128/863, 848, 857, 861, 859; 433/34, 36, 433/37, 5, 6, 7; 601/6
See application file for complete search history.

(56) References Cited

U.S. PATENT DOCUMENTS

| | | | | | |
|---|---|---|---|---|---|
| 3,236,235 | A | * | 2/1966 | Jacobs | 128/862 |
| 4,083,078 | A | * | 4/1978 | Shimizu | 15/244.1 |
| 4,955,393 | A | * | 9/1990 | Adell | 128/859 |
| 2006/0207610 | A1 | * | 9/2006 | Anonsen | 128/859 |
| 2007/0017528 | A1 | * | 1/2007 | Osterberg | 128/844 |
| 2007/0151568 | A1 | * | 7/2007 | Maurello | 128/859 |

* cited by examiner

*Primary Examiner* — Patricia M Bianco
*Assistant Examiner* — Ophelia Hawthorne
(74) *Attorney, Agent, or Firm* — White-Welker & Welker, LLC

(57) ABSTRACT

The present invention is an oral device comprised of two main components, a U-shaped lower bite plate and a U-shaped upper bite plate, which are molded to fit the front teeth of a wearer with a soft flexible contact surface. The oral device of the present invention comprises an upper bite plate and a lower bite plate each having a generally U-shaped appearance. The upper bite plate removably fits over the upper teeth of a person and the lower bite plate removably fits over the lower teeth of a person. Each bite plate includes a U-shaped buccal side and a U-shaped lingual side connected by a U-shaped top portion. The U-shaped top portion is further comprised of an exposed surface and an attaching surface where the exposed surface is the surface that contacts a penis, clitoris, or other body part while the attaching surface contacts the wearer's teeth.

13 Claims, 21 Drawing Sheets

ORAL DEVICE

FEDERALLY SPONSORED RESEACH

Not Applicable

SEQUENCE LISTING OR PROGRAM

Not Applicable

CROSS REFERENCE TO RELATED APPLICATIONS

Not Applicable

TECHNICAL FIELD OF THE INVENTION

The present invention relates generally to an oral device that is positionable over the teeth of a person while performing oral sex. More specifically, the present invention relates to an oral device positionable over the teeth of a person while performing oral sex that is molded to fit the front teeth with an attached soft interchangeable pads or series of attached soft interchangeable pads.

BACKGROUND OF THE INVENTION

A common complaint during fellatio is that the teeth scrape the penis, causing discomfort or pain. Typically the lips are used to cover the teeth, but this can be uncomfortable and difficult to sustain for extended periods of time. Additionally, it is the broad pressure applied by the extended lips along with the lubrication of saliva that provides a significant amount of the desirable stimulation during fellatio.

Oral prophylactic devices are well known in the prior art for use during oral sex. Typically, these devices perform the function of preventing the spread of diseases, such as the HIV virus and herpes. To accomplish this disease preventing function, the oral prophylactic devices known in the prior art are made of an impermeable plastic or rubber material that must be washed after use and can be uncomfortable to wear and use. Further, the use of a plastic material that is relatively hard, can also cause discomfort for both the giver and receiver.

For example, U.S. Pat. No. 4,949,731 to Harding discloses an oral prophylactic device wherein a tubular portion is received in the mouth and has a labial portion that fits over the person's lips. Both are also elastic and flexible to accommodate the natural range of movement of the lips, mouth and tongue. The purpose of the device is to prevent the spread of disease, such as AIDS.

Other devices which disclose oral prophylactic device for oral-genital use, and which are intended to prevent the passage of venereal and other disease are disclosed in U.S. Pat. No. 5,318,043 to Burr, et al.; U.S. Pat. No. 5,409,016 to Bloodsaw; U.S. Pat. No. 5,582,187 to Hussey; and U.S. Pat. No. 5,657,765 to Est.

All of these patents require an absolute shield between the consenting adult partners so that no bodily fluid is exchanged from one partner to the other partner. None of these patents allow the partners to be able to directly contact each other partner's body parts and body fluids between partners already knowing the other partner's health condition. All of these patents cover scenarios when there is a risk of passing a sexually transmitted disease. For example, long married partners would not have a desire for these devices when they wish to use an aid that enhances the oral sexual activity by not restricting contact between the partner's body parts and body fluids.

One shortcoming of the oral prophylactic devices known in the prior art is that they are pre-formed into exact shapes and dimensions, and will not conform to the different sized mouths and various sized teeth of various users.

Another shortcoming is that many of these devices, while flexible, do not provide a cushioned surface or lubrication, and can be both uncomfortable and harmful to the soft human tissue that the devices contact.

Yet another shortcoming is that many of these devices, while having different surfaces, do not have interchangeable options for providing different surfaces that would result in a variety of sensations for the wearer and any receiving partners.

SUMMARY OF THE INVENTION

The present invention is an oral device comprised of two main components, a U-shaped lower bite plate and a U-shaped upper bite plate, which are fitted to fit the front teeth of a wearer. The design and function of bite plates or dental beds are well known in prior art. Both the upper and lower bite plates have a soft flexible contact surface. The oral device of the present invention comprises an upper bite plate and a lower bite plate each having a generally U-shaped appearance. The upper bite plate removably fits over the upper teeth of a person and the lower bite plate removably fits over the lower teeth of a person. Each bite plate includes a U-shaped buccal side and a U-shaped lingual side 5 connected by a U-shaped top portion. The U-shaped top portion is further comprised of an exposed surface and an attaching surface where the exposed surface is the surface that contacts a penis, clitoris, or other body part while the attaching surface contacts the wearer's teeth. In an alternative embodiment where the oral device of the present invention covers a smaller number of upper and lower teeth, the device may appear to have ac-shaped appearance. Throughout the document, it should be noted that U-shaped and C-shaped reference the bite plate of the oral device whose appearance as U or C shaped is only a matter of size in the specific embodiment discussed.

It is an objective of the present invention to provide a removable, sanitary means for eliminating abrasion and scratching during oral sex as performed on a man by providing a wearable oral device that attaches to the teeth.

In addition, it is the objective to increase the amount of stimulation and type of stimulation by providing a broader contact area than would commonly be found by teeth or lip-covered teeth. The present invention, given its softness and use of available saliva as lubricant, would enable increased pressure over a larger area of the penis at any given time.

It is also an objective of this invention to provide the availability of a variety of tactile sensations.

It is also an objective of the present invention to significantly increase the range of pressure that could be applied during fellatio. Since the lips are no longer needed to cover the teeth, they add to the overall area stimulated, thus doubling the overall stimulation.

It is another objective of the present invention to provide a sanitary means for increasing female enjoyment and arousal during oral sex by providing a wearable oral device that attaches to the teeth of another person enabling them to straddle the clitoris from above and below and/or provide other enjoyable sensations. This embodiment of the invention utilizes a pad with a stiffer protrusion described as an inverted arc that when pressed against the opposing pad with its inverted arc allows for a tight cupping of the clitoral hood, enabling the clitoral hood to be pushed back, thus opening the clitoris for direct stimulation.

The pads, which may be permanently attached or interchangeable, are attached by a variety of methods. These interchangeable methods include barbed protrusions which lock the pad on the bite plate, rails on the bottom of the pad or the top of the bite bed that match cutouts allowing the pads to be slid on or off. The surfaces may also be permanently mounted by glue, any other form of fusion, or molded as one piece.

BRIEF DESCRIPTION OF THE DRAWINGS

The accompanying drawings, which are incorporated herein and form a part of the specification, illustrate the present invention and, together with the description, further serve to explain the principles of the invention and to enable a person skilled in the pertinent art to make and use the invention.

DETAILED DESCRIPTION OF THE INVENTION

In the following detailed description of the invention of exemplary embodiments of the invention, reference is made to the accompanying drawings (where like numbers represent like elements), which form a part hereof, and in which is shown by way of illustration specific exemplary embodiments in which the invention may be practiced. These embodiments are described in sufficient detail to enable those skilled in the art to practice the invention, but other embodiments may be utilized and logical, mechanical, electrical, and other changes may be made without departing from the scope of the present invention. The following detailed description is, therefore, not to be taken in a limiting sense, and the scope of the present invention is defined only by the appended claims.

In the following description, numerous specific details are set forth to provide a thorough understanding of the invention. However, it is understood that the invention may be practiced without these specific details. In other instances, well-known structures and techniques known to one of ordinary skill in the art have not been shown in detail in order not to obscure the invention.

Referring to the figures, it is possible to see the various major elements constituting the apparatus of the present invention. The invention is an oral device comprised of two main components, a U-shaped lower bite plate and a U-shaped upper bite plate, which are molded to fit the front teeth of a wearer with a soft flexible contact surface.

Figure 1:
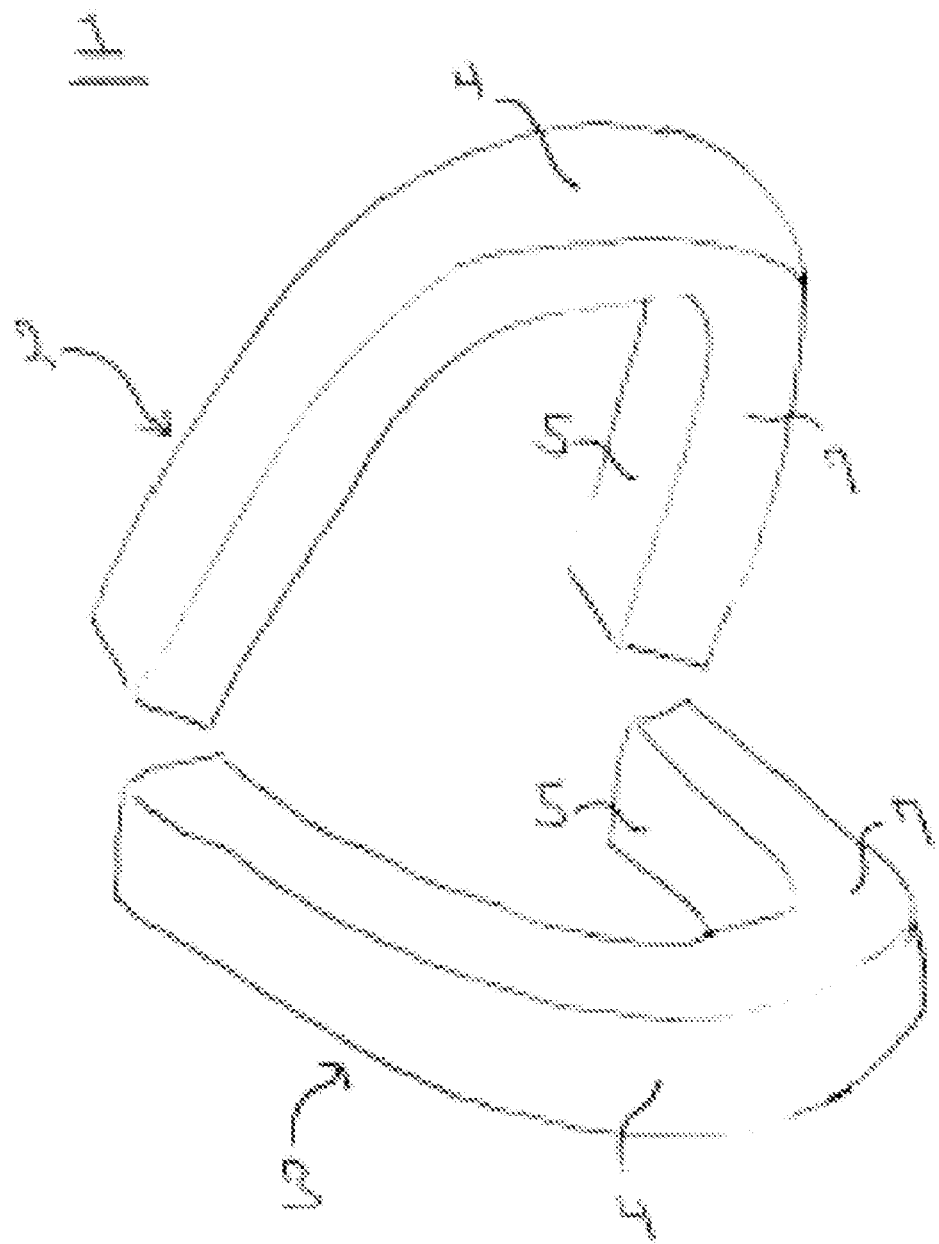
FIG. 1 is a perspective view of the oral device of the present invention.

Now referring to FIG. 1, a first embodiment of the present invention is illustrated where an oral device 1 comprising an upper bite plate 2 and a lower bite plate 3 each having a generally U-shaped appearance. The upper bite plate 2 removably fits over the upper teeth of a person and the lower bite plate 3 removably fits over the lower teeth of a person. Each bite plate 2 & 3 includes a U-shaped buccal side 4 and a U-shaped lingual side 5 connected by a U-shaped top portion 6. The U-shaped top portion is further comprised of an exposed surface 7 and an attaching surface 8 where the exposed surface 7 is the surface which contacts a penis, clitoris, or other body part while the attaching surface 8 contacts the wearers teeth.

Figure 2:
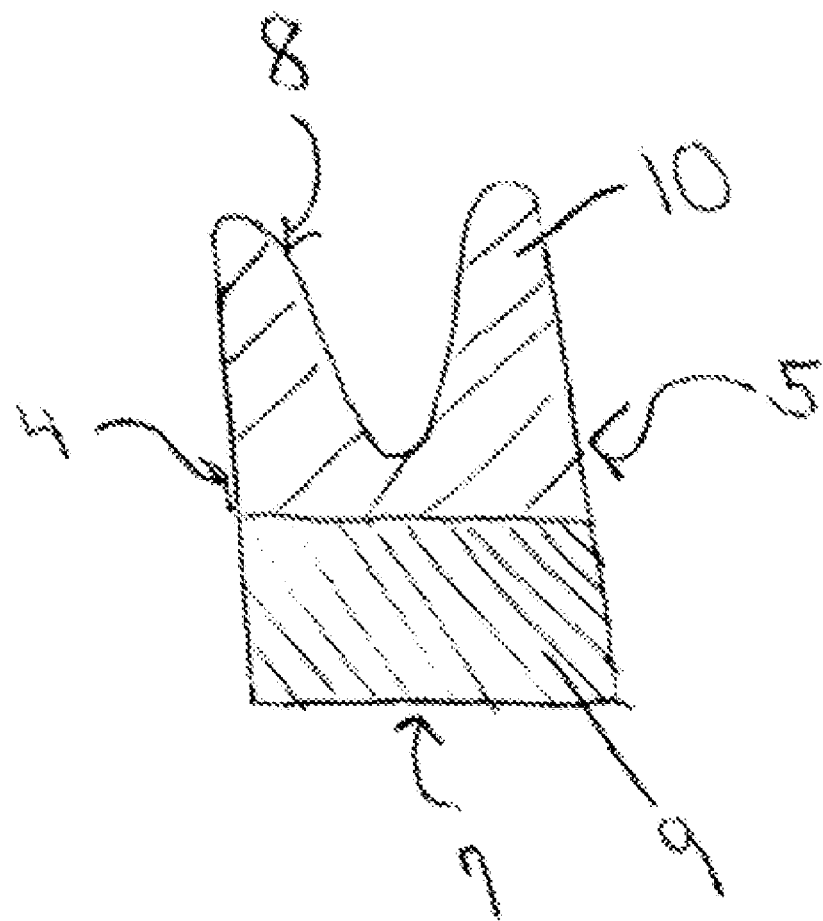
FIG. 2 is a cross section view of a bite plate of the present invention.

Now referring to FIG. 2, the attaching surface 8 is molded to fit the upper or lower teeth of a person and is preferably constructed from a material that is only flexible enough to provide a compression force from the attaching surface 8 when it is lightly forceably pushed into placed on a persons teeth to sufficiently attach the device during oral sex. The attaching surface is defined by a sloping valley in similar shape and size to that of a persons tooth. In an alternative embodiment, the attaching surface 8 is made from a moldable material 10 similar to that known in the prior art which may be heated in boiling water, placed in a users mouth for some short period of time and then allowed to cool, resulting in a custom molded attaching surface 8 that is identical to that of the person who created the mold, the assumed user or wearer of the device. In addition there are other methods commonly used by the dental industry to create similar temporary bonding opportunities that may be enjoyed by the present invention.

Still referring to FIG. 2, the cross-sectional view illustrates that two different materials are comprised to make a bite plate. Preferably the top portion 6 is made from a softer more flexible material 9 than that of the attaching surface 8, which molds to the teeth. The softer more flexible material 9 used must be present to provide the shielding effect for both the upper and lower teeth.

The device of the present invention may vary in size. As illustrated in FIG. 1, the oral device is large enough to cover the complete dental plate of a person. It is generally acknowledged that protection during oral sex given to a man only requires protection from abrasion caused by the central and lateral incisors, and possibly the canine teeth. In fact, variations of the design would allow for models that just covered these teeth alone, or additional teeth or some lesser number of teeth. Thus, it would be obvious to one of ordinary skill in the art to modify the size of the bite plates 2 & 3 as necessary or desired.

Figure 3:
FIG. 3 is a perspective view of a specific alternative embodiment of the oral device of the present invention for use on women is illustrated.
Figure 3:
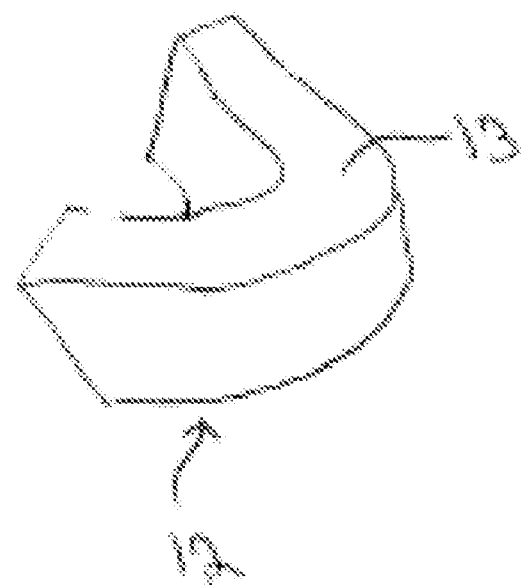
Figure 4A:
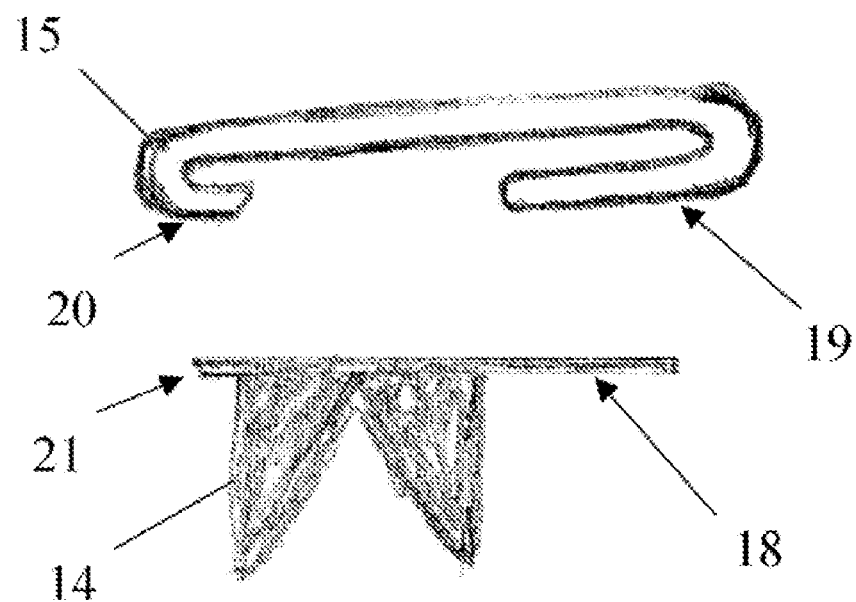
FIGS. 4a-4b illustrates preformed pads that wrap around or snap around the tooth bed with additional protrusions providing extra surface area or lip covering.
Figure 4B:
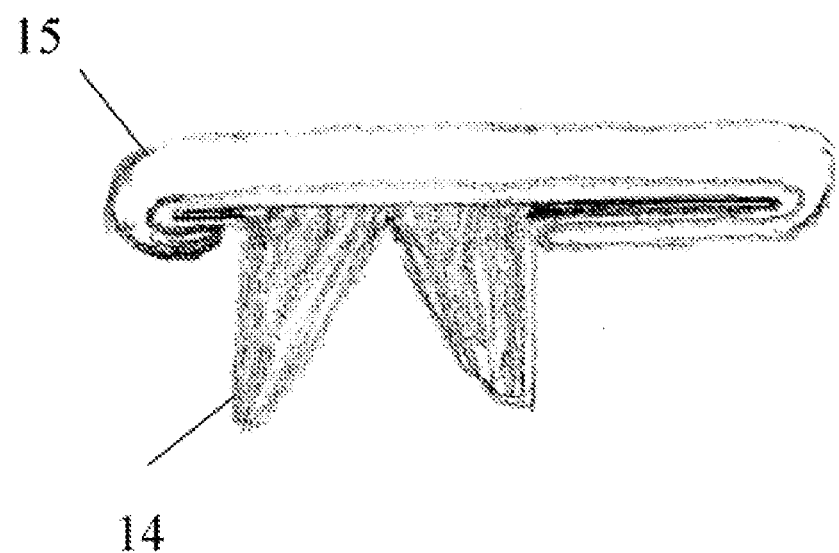

Now referring to FIG. 3, a specific alternative embodiment of the present invention is illustrated for use on women. To straddle the clitoris from below and above the bite plates 11 & 12 are only large enough to cover the central incisors and the device preferably has a firmer exposed surface 13 for use on a woman than that embodiment for use on a man.

Now referring to FIGS. 4-10, a preferred and alternative embodiments of pad securing means for the use of interchangeable and/or removable pads and surfaces is illustrated. In FIG. 4a-4b a U-shaped bite plate 14 is shown which includes a flat top portion 21. The flat top portion 21 is further comprised of two opposing protrusions 18 and 21. In this embodiment a preformed pad 15 with c shaped ends 20 and 19 is utilized. The preformed pad snaps over the bite plate in such a manner that the two opposing protrusions 18 and 21 of the flat top portion 21 of the bite plate 12 interlock with the c shaped ends 20 and 19 of the preformed pad 15. As illustrated, one end of the bite plate 14 and pad 15 may be comprised of a longer protrusion 19 and 18. Longer protrusions may be desired to provide protection of the lips or to increase surface area.

Figure 5A:
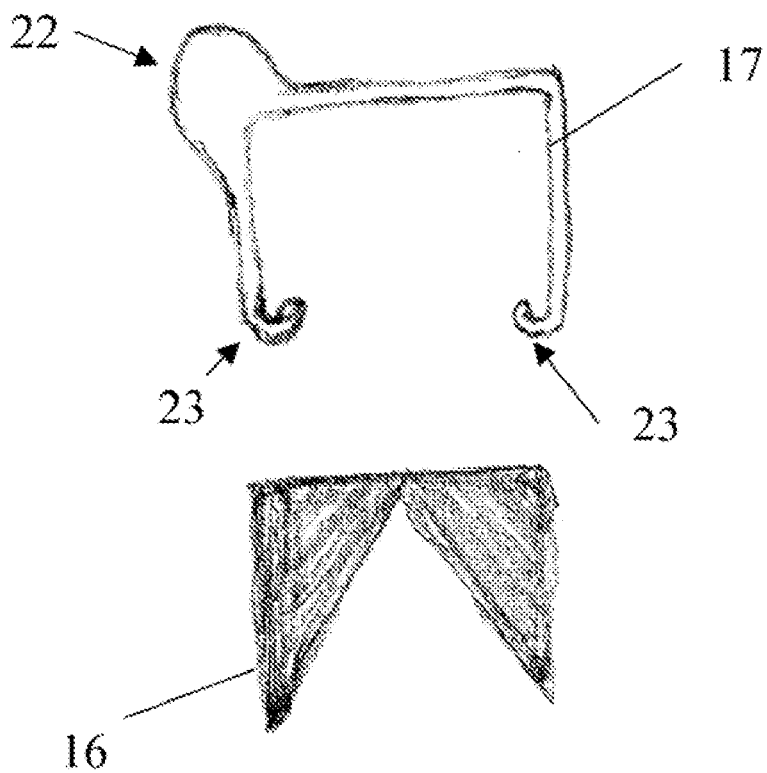
FIGS. 5a-5b illustrates preformed pads that wrap around the tooth bed and attach at the bottom of the tooth bed with a protrusion.
Figure 5B:
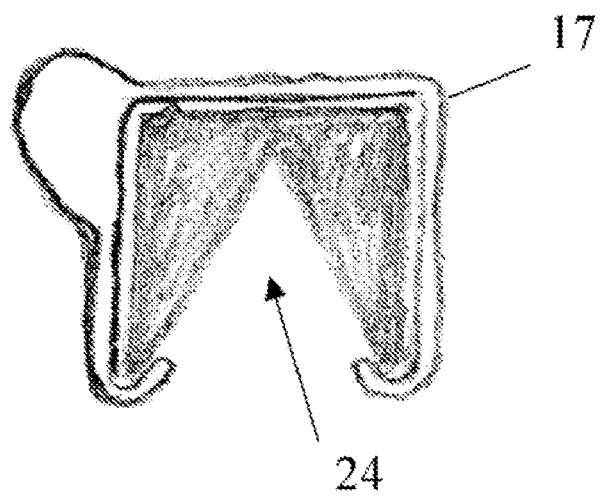

Now referring to FIG. 5, a preformed pad 17 is illustrated that contains a rounded protrusion 22 and hooks 23 for connect around the sides of a bite plate 16.

Figure 6A:
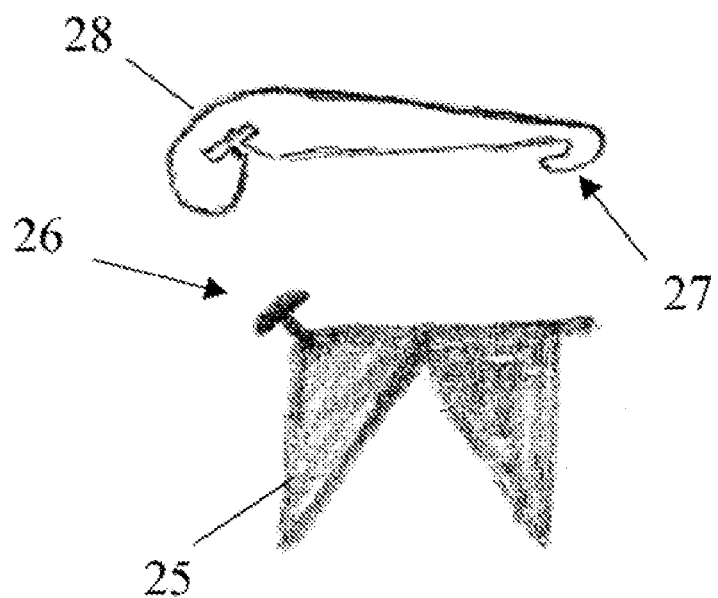
FIGS. 6a-6b illustrates attachment via a 'T' rail in addition to wrapping around a protruding edge.
Figure 6B:
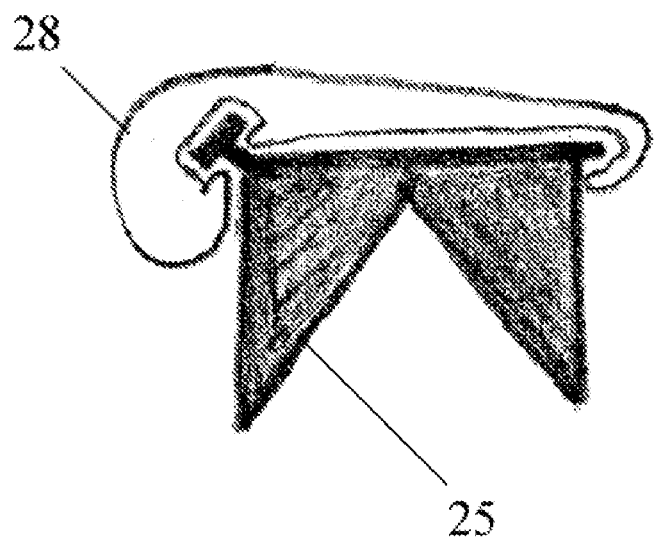
Figure 7A:
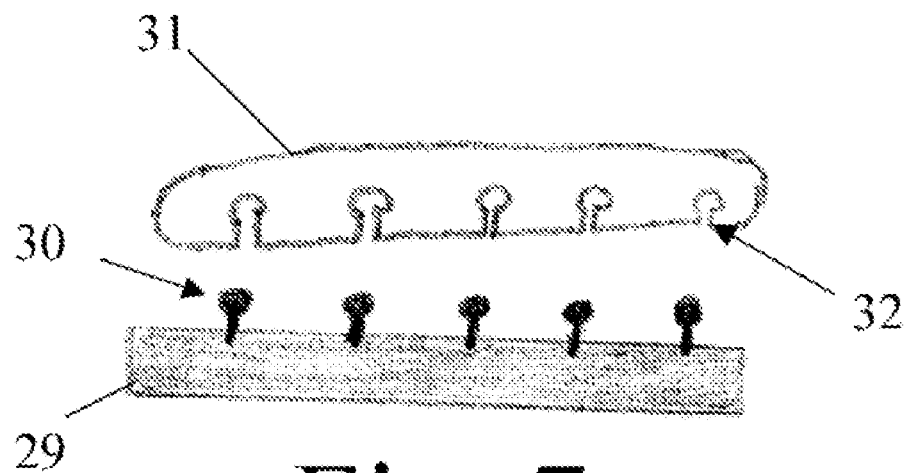
FIGS. 7a-7b illustrates attachment by posts with barbs or balls that lock into an opening on the pad surface.
Figure 7B:
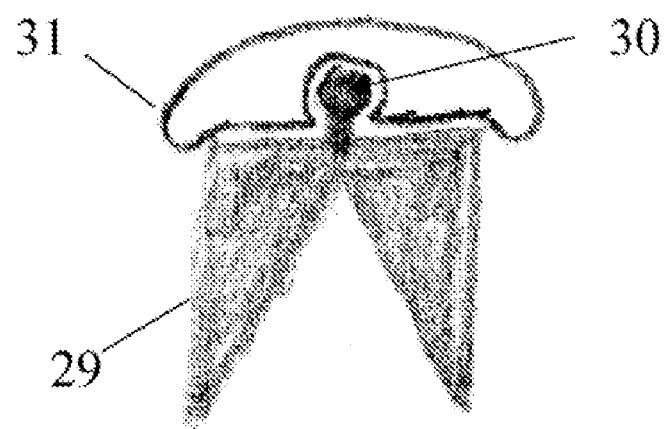
Figure 9A:
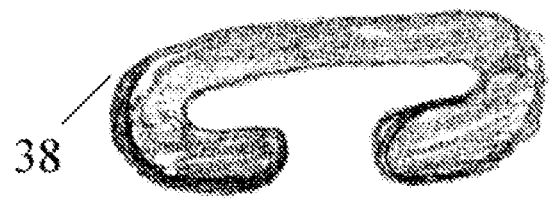
FIGS. 9a-9b illustrates a protruding 'T' rail that provides means for securing pads wrapped around or slid on its surface.
Figure 9A:
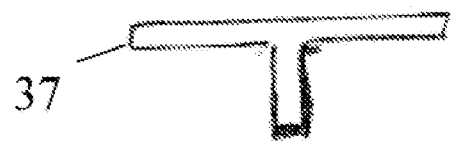
Figure 9B:
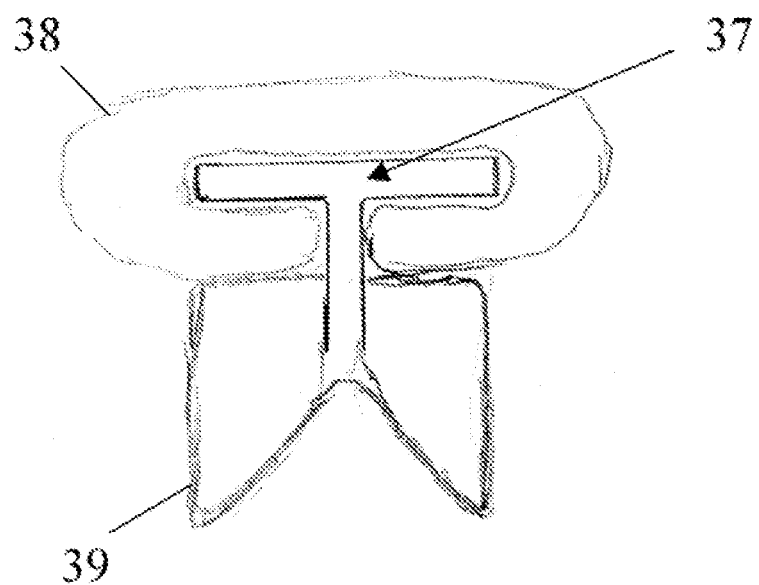
Figure 10A:
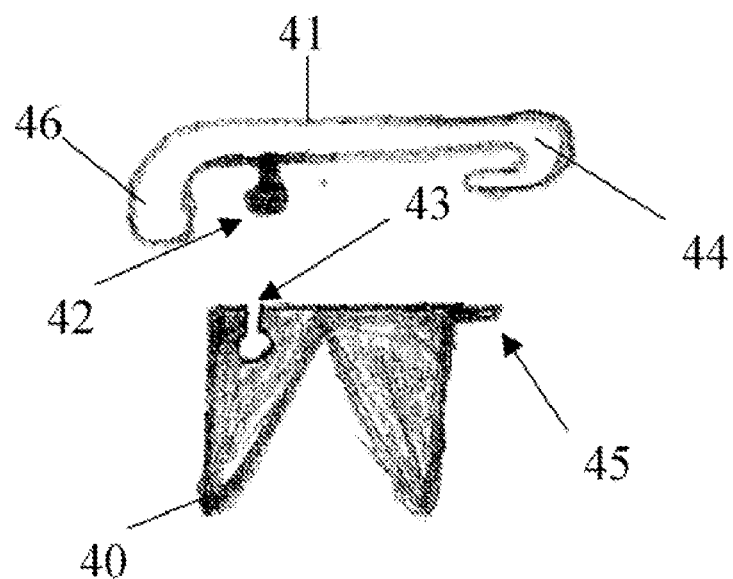
FIGS. 10a-10b illustrates a key and keyhole rail style of mounting, in combination with a wrapping around of a pad to an interior protrusion.
Figure 10B:
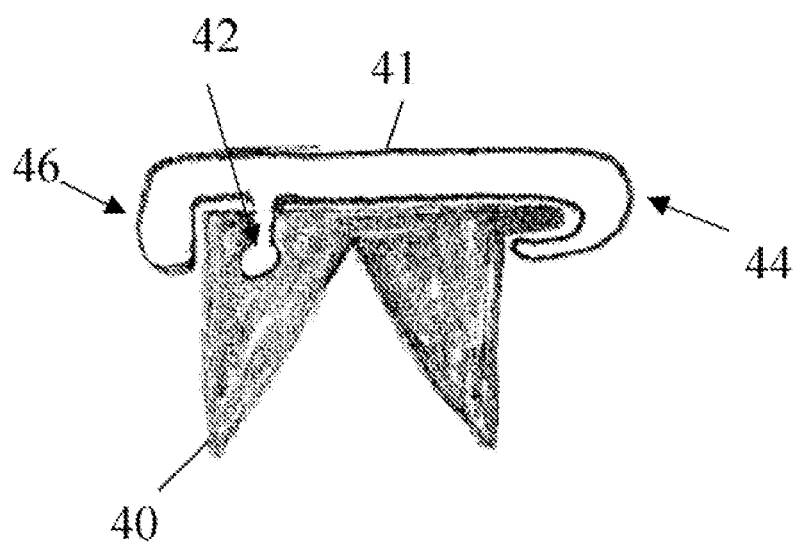
Figure 11A:
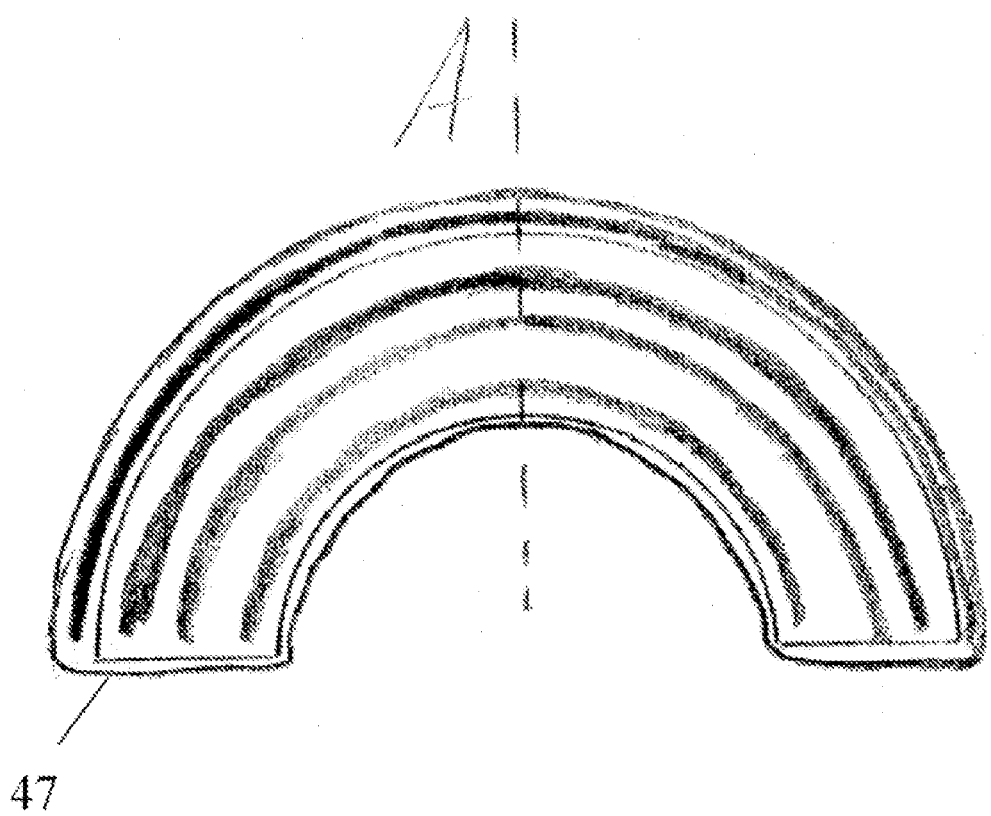
FIGS. 11a-11b illustrates a ribbed pad comprising a protruding surface toward the lips.
Figure 11B:
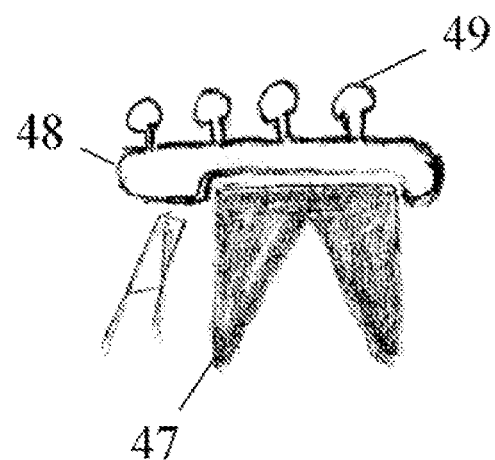

FIGS. 6a-6b and 9a-9b illustrate the use of a "T" rail system for attaching preformed pads 28 to bite plates 25. Referring to FIGS. 6a-6b, a "T" rail 26 is attached to one corner of the bite pate 26 while the preformed pad 28 is comprised of a female "T" rail recess 24 and rear hook 27 for attachment to a protruding edge of the bite pad 25. In FIGS. 9a-9b a larger "T" rail 37 is positioned on the top surface of the bite plate 39 and a preformed pad 38 with a corresponding "T" shaped recess wraps around the "T" rail 37 to secure the pad 38 to the bite plate 39. Now referring to FIGS. 7a-7b and 10a-10b an alternative attachment means is illustrated where a plurality of posts with a barb or ball end 30 extending from the bite place 29 locks into a plurality of corresponding recesses 32 in a preformed pad 31. As shown in FIGS. 9a-9b, the posts 30 can be centered in the bite plate 29 and extend for the length of the pad 31 or, as illustrated in FIG. 10a-10b the recesses 42 can be placed toward one side of the top surface of the bite plate 40 and the bite plate can have a rear protrusion. In this embodiment, the preformed pad would contain the plurality of posts with a barb or ball end 42, have one rolled edge 46 and one wrap around edge 44 for securing the preformed pad 41 to the protrusion 45 on the bite plate 40.

Figure 8A:
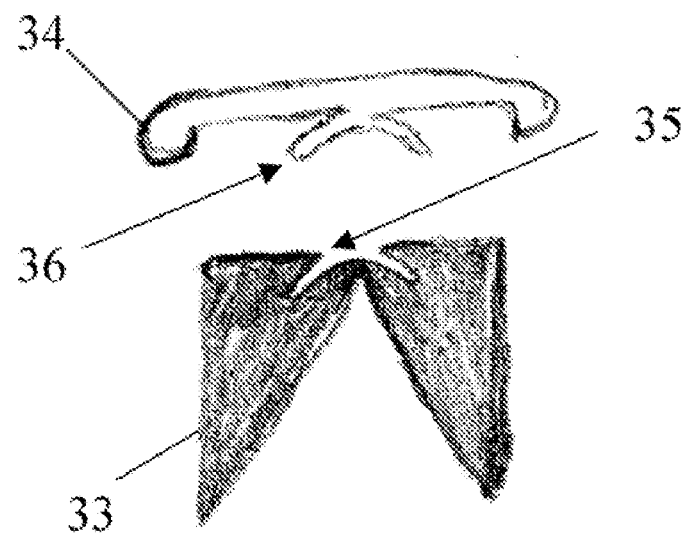
FIGS. 8a-8b illustrates an alternative rail mounting system.
Figure 8B:
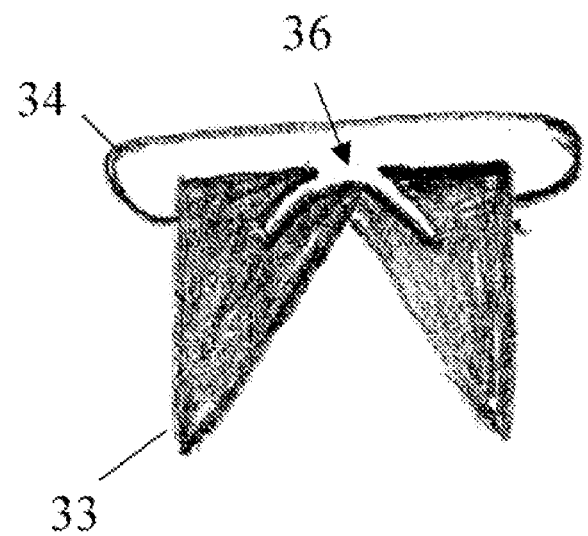

FIG. 8a-8b illustrates another embodiment utilizing a key 36 and keyhole 35 rail style of mounting, in combination with a wrapping around of the preformed pad 34 to a protrusion on both ends of the bite plate 33. In all of the embodiments, the material of choice is a pliable version of silicon, but it is recognized that anyone of ordinary skill in the art would readily be able to determine the best silicone or equivalent compound for use in the bite plate and preformed pads.

In a preferred embodiment of the oral device or the present invention, the exposed surface is described as being as twice as broad as a typical lip, with a texture and softness comparable to the exposed surface of a human lip. It is further described as smooth, firm, but with a depth of 'give'.

The exposed surface can also be broader or skinnier, allowing for more or less exposed surface than the previous description, allowing increased or decreased contact area. The texture of the exposed surface can be smooth or roughened with bumps, ridges, grooves, or other variations designed to provide different tactile sensations. The pad can be dense allowing for a firmer feel or less dense, allowing for a softer feel. The profile of the pad can be flat as described or curved on the sides to increase contact area. The pad can be designed like a sponge so as to allow the release of a flavoring additive.

The concept of interchangeable pads allows for various shapes and surfaces to be added to the bite plates. For example pads of different softness, pads with sponge like characteristics which could be designed to release flavor, pads with upward flaring outer edges to increase stimulation around the sides or pads with bumps or grooves to increase friction. A pad made of thick stretchy material could be attached to both the upper and lower bite plates. A pad with a small hole in the middle would provide stimulation completely around the penis.

The pads, which may be permanently attached or interchangeable, are attached by a variety of methods. These interchangeable methods include barbed protrusions which loc the pad on the bite plate, rails on the bottom of the pad or the top of the bite bed that match cutouts allowing the pads to be slid on or off.

Now referring to FIGS. 11-20, a preferred and alternative embodiments of exposed surfaces are illustrated. Referring now to FIGS. 11a-11b a preformed pad 48 with a plurality of ribs 49, and a protruding portion toward the lips of a wearer is illustrated as mounted to a bite plate 47. FIGS. 14a-14b illustrate a similar embodiment wherein the protrusion 59 of the preformed, thicker and lower density pad 58 attached to the bite plate 57 is longer, to completely cover the lips of a wearer.

Figure 12A:
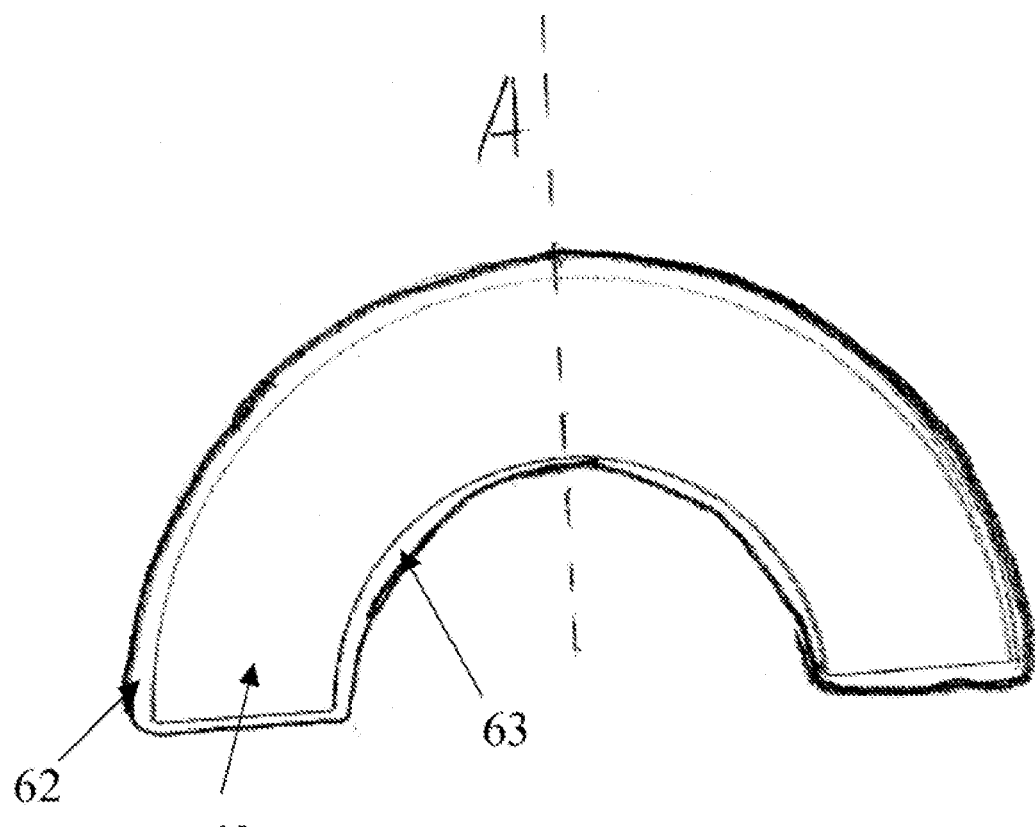
FIGS. 12a-12b illustrate thinner higher density pads.
Figure 12B:
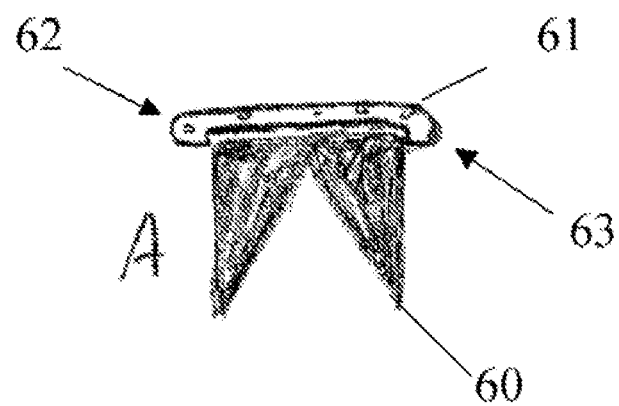
Figure 13A:
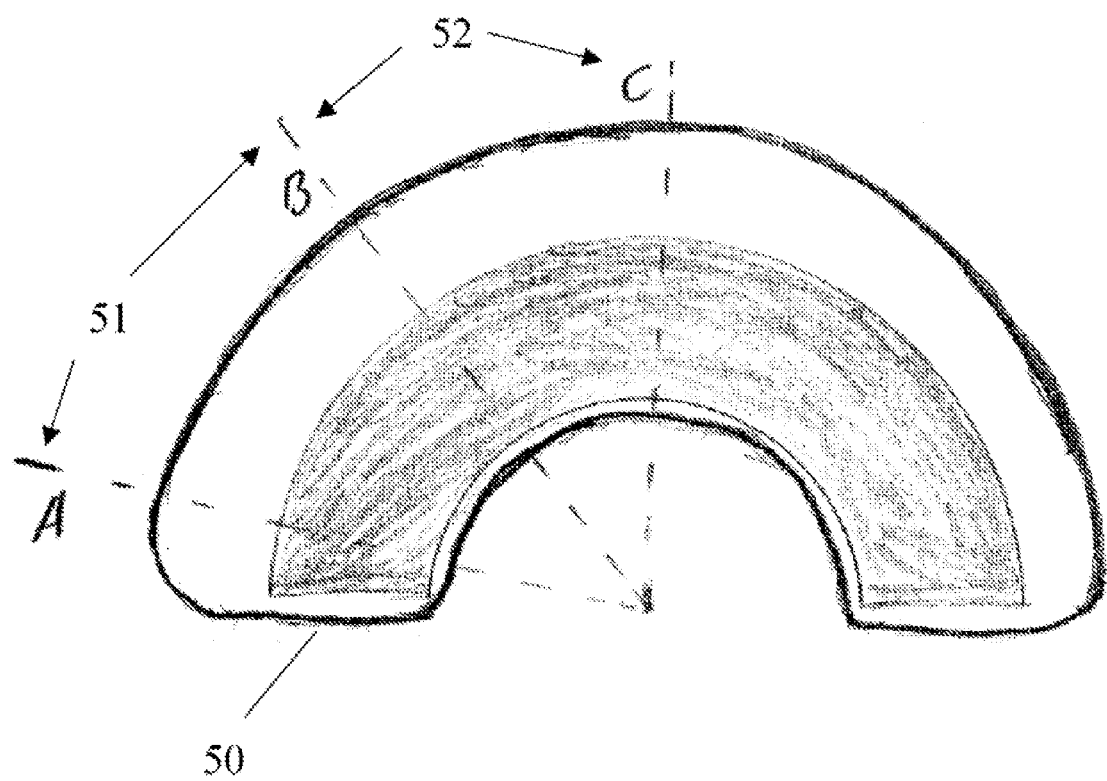
FIGS. 13a-13d illustrate pads with various curved or flared protruding surfaces.
Figure 13B:
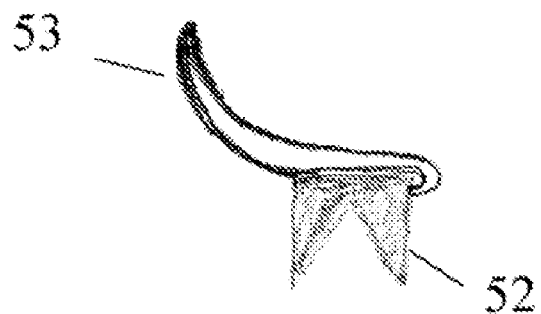
Figure 13C:
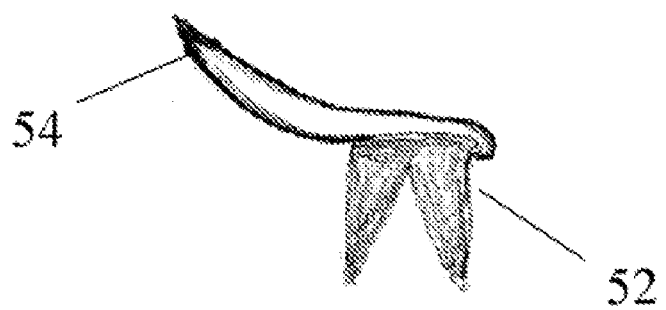
Figure 13D:
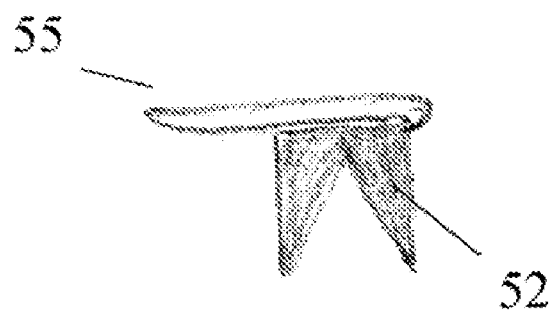
Figure 14A:
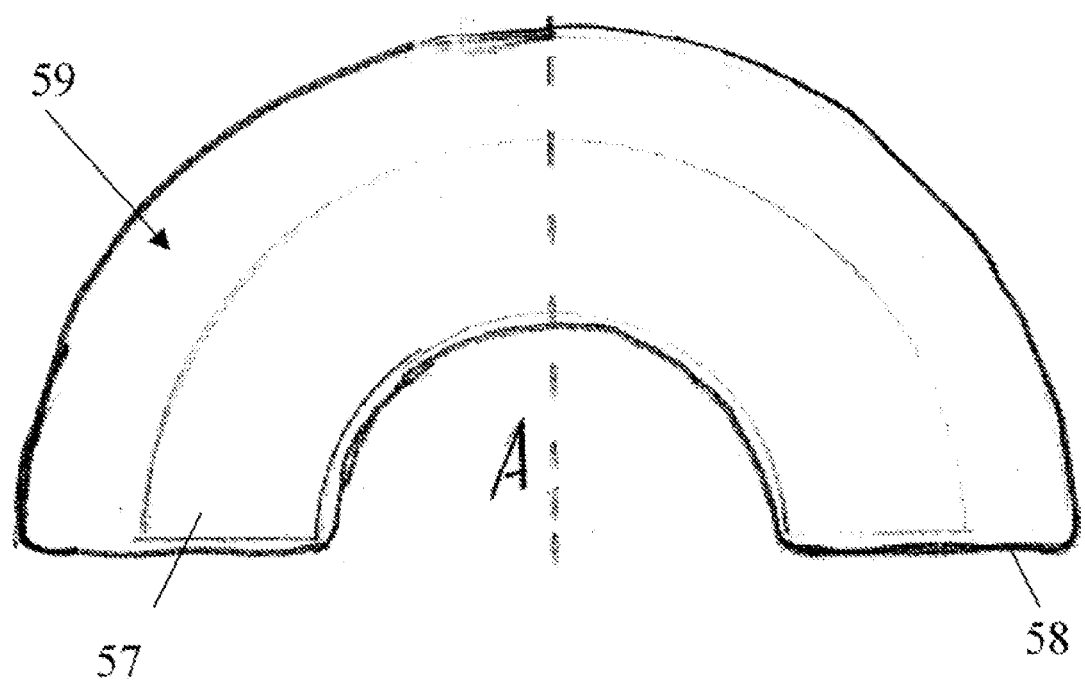
FIGS. 14a-14b illustrate thicker lower density pads with a flat protruding surface toward the lips.
Figure 14B:
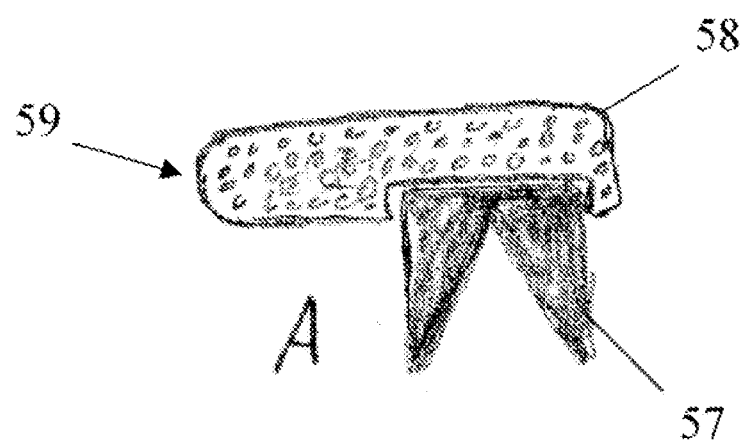

FIGS. 12a-12b illustrate a thinner, higher density flared pad 61 that has two flared edges 62 and 63 to diminish the likely hood of contact with the bite plate 60. Conversely FIGS. 13a-13d illustrate a bite plate 52 with multiple preformed pads attached 53, 54 and 55. As illustrated pads 53, 54, and 55 can have any angle of curve to their protrusion from a flat protrusion 55, a 45 degree protrusion 54, and a 60-80 degree protrusion 53. The pads can be attached in any order or in sectional grouping such as those denoted by sections A, B, and C on FIG. 13a. In an alternative embodiment, FIGS. 13b-13d can also illustrate a single pad attached to a bite plate 52 with varying degrees and lengths of flaring from a flat protrusion 55, a 45 degree protrusion 54, and a 60-80 degree protrusion 53.

Figure 15A:
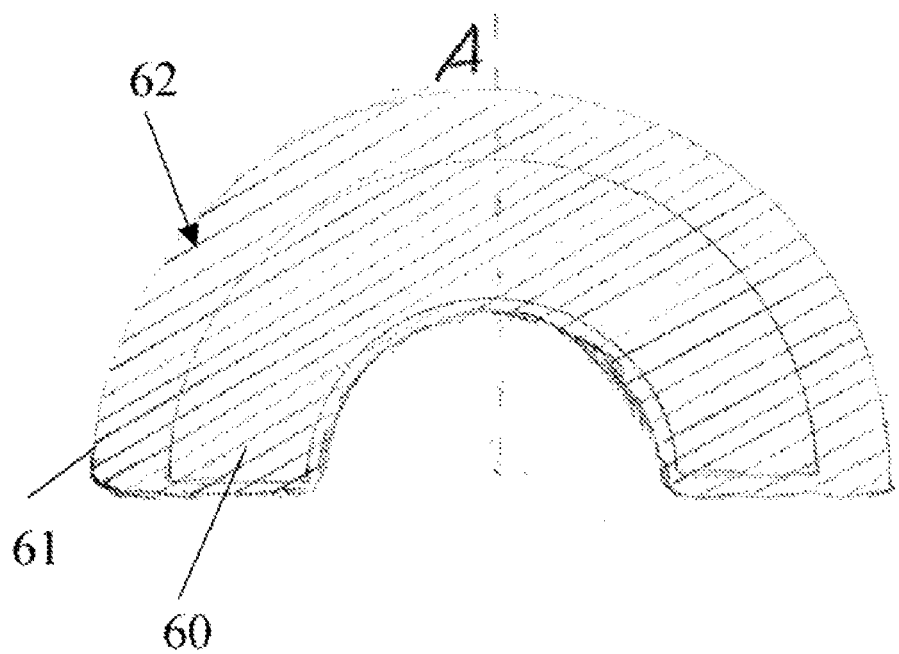
FIGS. 15a-15b illustrates grooved pads with a flat protruding surface toward the lips.
Figure 15B:
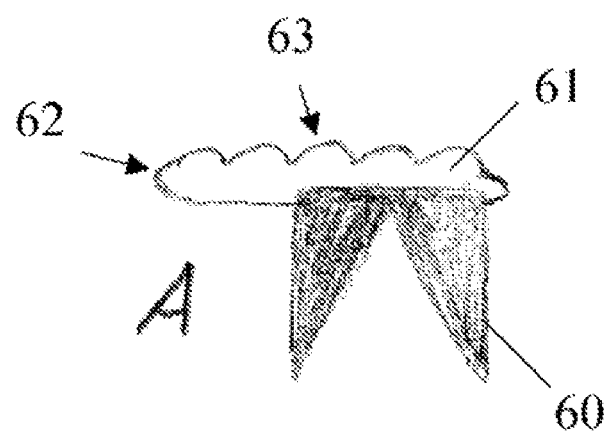
Figure 16A:
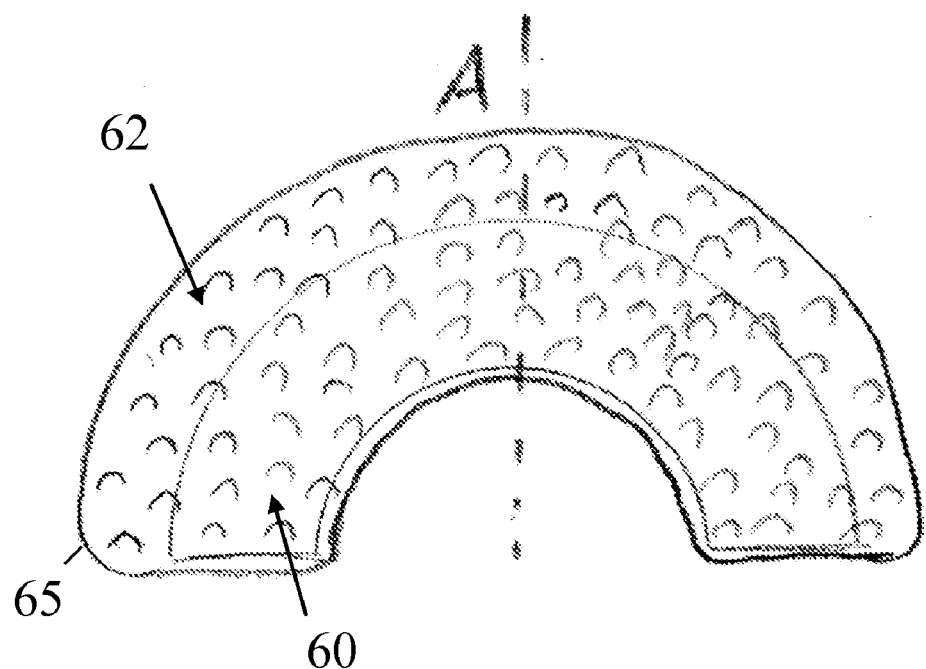
FIGS. 16a-16b illustrates bumpy pads with a flat protruding surface toward the lips.
Figure 16B:
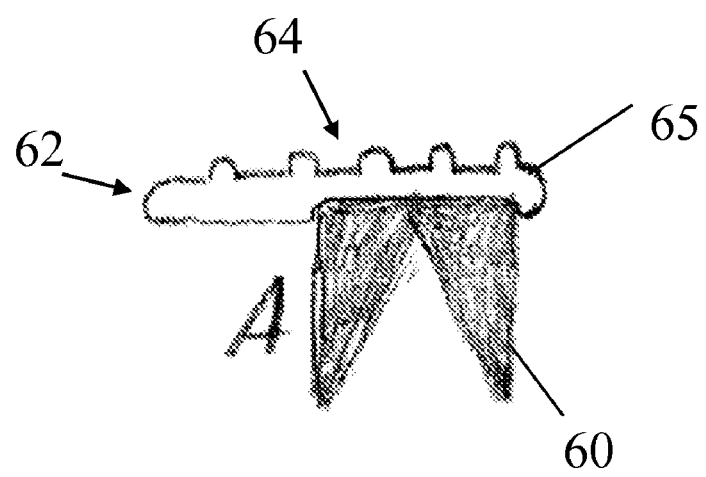
Figure 17A:
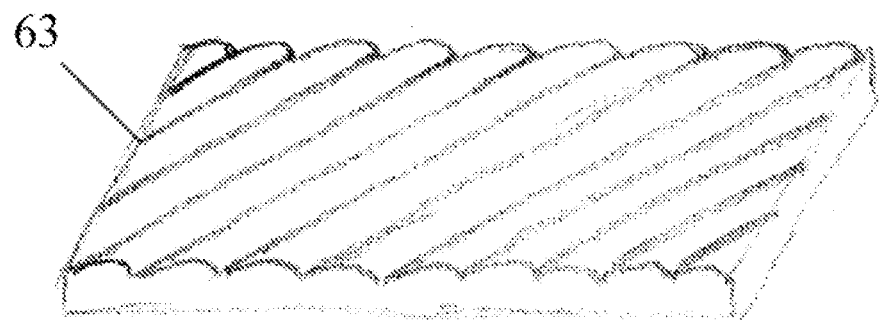
FIGS. 17a-17c illustrates a variety of pad surfaces used in the present invention.
Figure 17B:
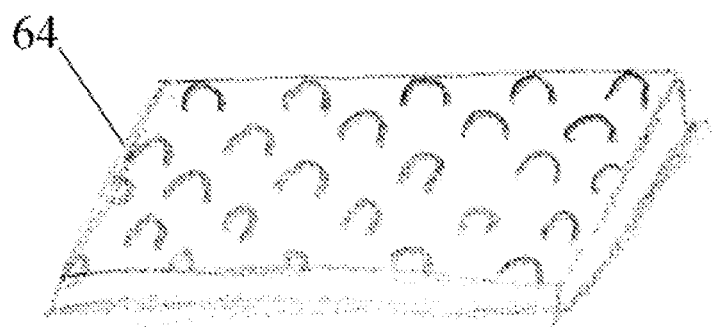
Figure 17C:
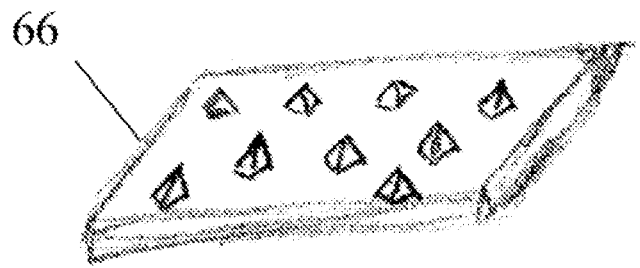

Referring not to FIGS. 15a-15b, 16a-16b, and 17a-17c a few alternative embodiments of pad surfaces utilized by the present invention are disclosed. In FIGS. 15a-15b and 17a a preformed pad 61 with a grooved surface 63 is shown with a protrusion 62, as attached to a bite plate 60 before use. FIGS. 16a-16b and 17b illustrate a bumpy pad 65 with rounded bumps 64 on its surface and a protrusion 62. In FIG. 17c a bumpy pad surface with sharper, pyramid shaped bumps 66 is illustrated as an alternative surface feature.

Figure 18A:
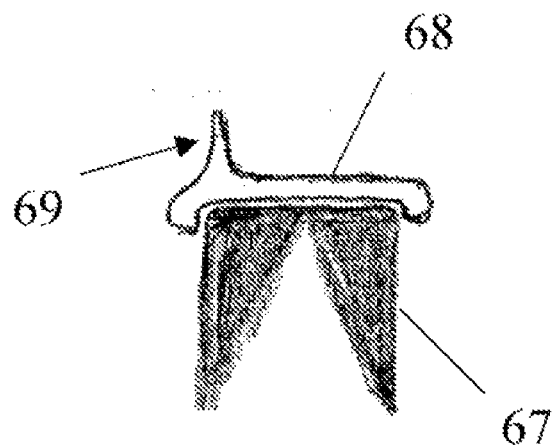
FIGS. 18a-18b illustrates a pad designed for clitoral hood retraction.
Figure 18B:
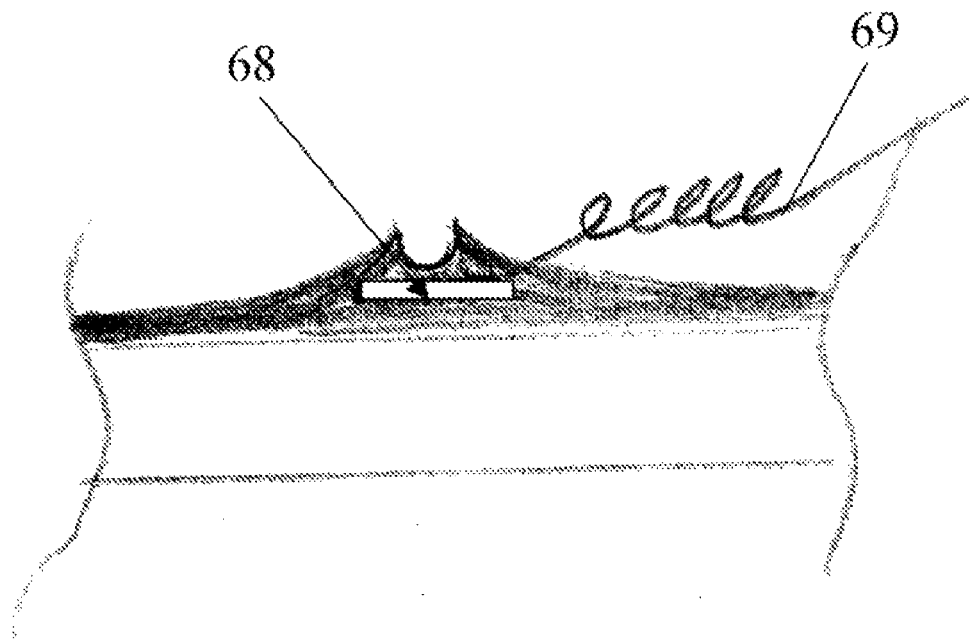

Now referring to FIGS. 18a-18b, in an alternative embodiment of the present invention a sanitary means for increasing female enjoyment and arousal during oral sex by providing a wearable oral device that attaches to the teeth of another person enabling them to straddle the clitoris from above and below and/or provide other enjoyable sensations is illustrated. This embodiment of the invention utilizes a preformed pad 68 with a stiffer protrusion 69 described as an inverted arc that when pressed against the opposing pad with its corresponding inverted arc allows for a tight cupping of the clitoral hood, enabling the clitoral hood to be pushed back, thus opening the clitoris for direct stimulation. A corded 69 or battery operative vibration means 68 could also be included in the preformed pad to provide further stimulation to the clitoral hood.

Figure 19A:
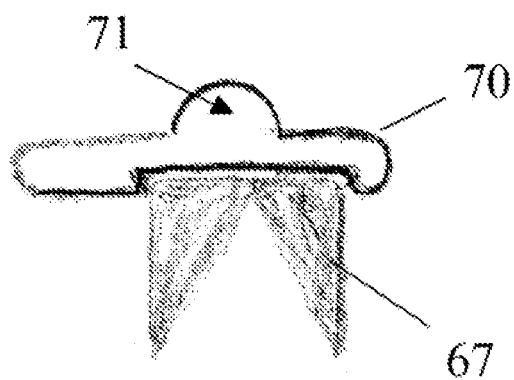
FIGS. 19a-19b illustrates a pad with a single central bump.
Figure 19B:
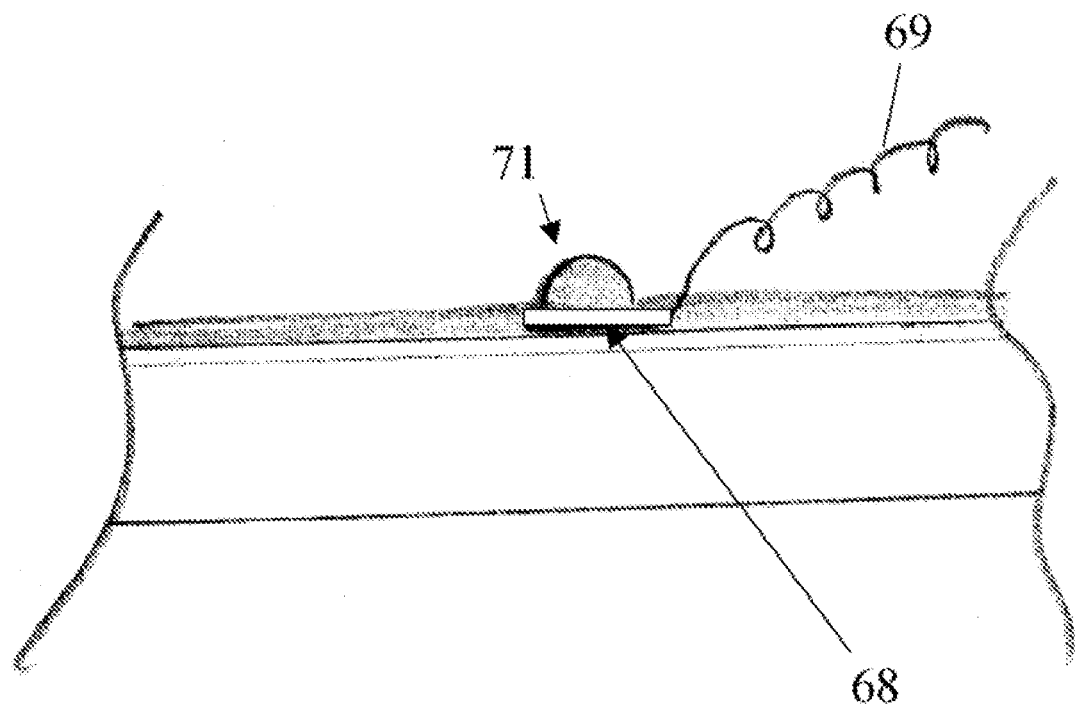

Now referring to FIGS. 19a-19a preformed pad 70 with a single central bump 71 is illustrated. This pad may or may not have an extended protrusion to cover a wearer's lips and also may be fixed with a corded 69 or battery vibration device 68.

Figure 20A:
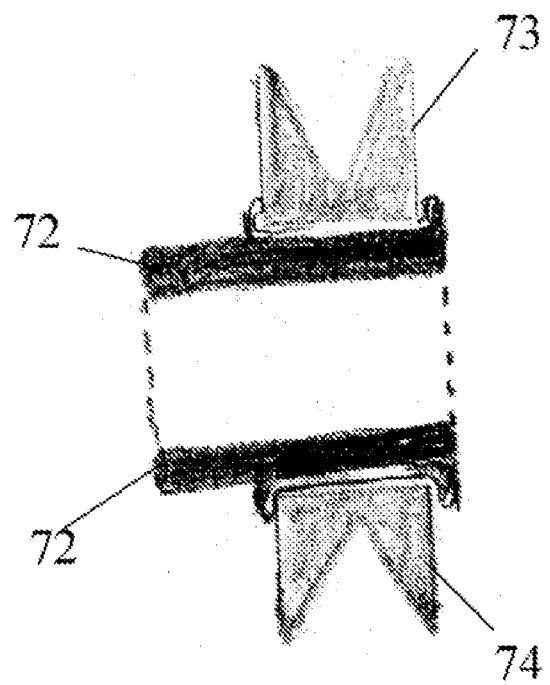
FIGS. 20a-20b illustrates an upper and lower tooth bed joined by a donut shaped pad.
Figure 20B:
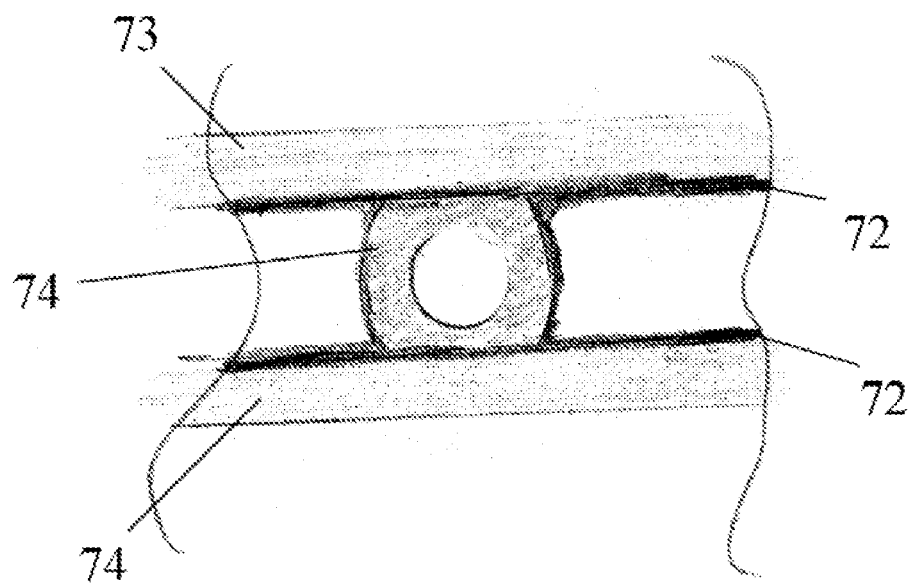

Referring to FIGS. 20a-20b a final alternative embodiment includes a donut shaped pad 74 that is secured between the upper bite plate 73 and lower bite plate 74, via preformed pads 72 with flaring edges, these preformed pads 72 may be larger or smaller than the bite plates 73 and 74, and may have varying density of firmness and heights.

The types of material used for the pad may be natural or man made, flesh-like or modified for firmer or softer feel. The utilization of the devices taught by the present invention could be one time disposable with a fixed pad, multiple use with a fixed pad, or multiple use with interchangeable pads.

Thus, it is appreciated that the optimum dimensional relationships for the parts of the invention, to include variation in size, materials, shape, form, function, and manner of operation, assembly and use, are deemed readily apparent and obvious to one of ordinary skill in the art, and all equivalent relationships to those illustrated in the drawings and described in the above description are intended to be encompassed by the present invention.

Furthermore, other areas of art may benefit from this method and adjustments to the design are anticipated. Thus, the scope of the invention should be determined by the appended claims and their legal equivalents, rather than by the examples given.

The embodiments of the invention in which an exclusive property or privilage is claimed are defined as follows:

1. An oral device comprising: a U-shaped lower bite plate molded to fit the front teeth of a wearer;
   said U-shaped lower bite plate consisting of
   a U-shaped lower buccal side;
   a U-shaped lower lingual side; and
   a U-shaped lower top portion thereby connecting the U-shaped lower buccal side and the U-shaped lower lingual side; and
   the U-shaped lower top portion is further comprised of an exposed surface and an attaching surface;
   a U-shaped upper bite plate molded to fit the front teeth of a wearer,
   said U-shaped upper bite plate consisting of
   a U-shaped upper buccal side;
   a U-shaped upper lingual side; and
   a U-shaped upper top portion thereby connecting the U-shaped upper buccal side and the U-shaped upper lingual side; and
   the U-shaped upper top portion is further comprised of an exposed surface and an attaching surface;
   a pad attached to the distal end of the upper bite plate; and
   a pad attached to the distal end of the lower bite plate; and
   wherein each pad surface includes a single central bump.

2. The oral device of claim 1 wherein the pads are interchangeable.

3. The oral device of claim 2 wherein the pads are attached by either:
   one or more barb like protrusions,
   one or more matching receptacles, or
   one or more sliding rails with matching grooves.

4. The oral device of claim 3 wherein a "T" rail is used.

5. The oral device of claim 3 wherein attachment of the pads to the bite plate is comprised of posts with a ball or barb that lock into a recessed opening on the pad.

6. The oral device of claim 2 wherein the pads are attached by-the edge of the preformed pad around a top protruding surface of the bite plate.

7. The oral device of claim 1 wherein the pads are further comprised of vibration means.

8. The oral device of claim 7 wherein each pad consists of a half donut shaped which forms a donut shaped opening when the upper and lower bite plates are together.

9. The oral device of claim 7 wherein the pads are permanently mounted by glue or other form of fusion.

10. The oral device of claim 1 wherein each pad consists of u-shaped protrusions over the central upper and lower teeth to cup the clitoral hood firmly.

11. The oral device of claim 1 wherein each pad is constructed from a sponge-containing flavoring for release during use.

12. The oral device of claim 1 wherein the profile of the pad is curved on one side to increase contact area with respect to the horizontal top portion of the bite plate.

13. The oral device of claim 1 wherein each pad is larger than the bite plate to which it is attached with respect to the horizontal top portion of the bite plate.

* * * * *